(12) United States Patent
Gratteau

(10) Patent No.: US 8,326,395 B2
(45) Date of Patent: Dec. 4, 2012

(54) ELECTRODE FOR ELECTRORETINOGRAPHIC USE AND METHOD OF APPLICATION

(76) Inventor: Jack Edward Gratteau, Morgan Hill, CA (US)

( * ) Notice: Subject to any disclaimer, the term of this patent is extended or adjusted under 35 U.S.C. 154(b) by 350 days.

(21) Appl. No.: 12/622,403

(22) Filed: Nov. 19, 2009

(65) Prior Publication Data

US 2011/0118584 A1    May 19, 2011

(51) Int. Cl.
*A61B 5/04* (2006.01)
(52) U.S. Cl. .......................... 600/383; 600/558
(58) Field of Classification Search .................. 600/383, 600/558
See application file for complete search history.

(56) References Cited

U.S. PATENT DOCUMENTS

| | | | |
|---|---|---|---|
| 4,131,113 A | 12/1978 | Fender | |
| 4,417,581 A | 11/1983 | Dawson | |
| 4,735,207 A | 4/1988 | Nambu et al. | |
| 4,874,237 A | 10/1989 | Cringle | |
| 5,154,174 A | 10/1992 | Hawlina | |
| 5,297,554 A | 3/1994 | Glynn et al. | |
| 7,384,145 B2 | 6/2008 | Hetling et al. | |
| 7,596,400 B2 | 9/2009 | Valjakka et al. | |

OTHER PUBLICATIONS

M. F. Marmor, A. B. Fulton, G. E. Holder, Y. Miyake, M. Brigell, and M. Bach; "ISCEV Standard for full-field clinical electroretinography", Doc Ophthalmol (2009) 118:69-77 Springer-Verlag.

William W. Dawson, Gary L. Trick, and Carl A. Litzkow; "Improved electrode for electroretinography", Invest. Ophthalmol. Visual Sci (Sep. 1979) vol. 18 No. 9, pp. 989-991 Assoc. for Res. in Vis. and Ophthal., Inc.

*Primary Examiner* — Lee S Cohen

(57) ABSTRACT

A flexible loop electrode for electroretinographic (ERG) recordings of extra-corneal signals with a protective bead and a U-shaped electrode form that is particularly adapted for use with spectacles or a fixed mount. Means also employed to detect electrode integrity.

17 Claims, 4 Drawing Sheets

ELECTRODE FOR ELECTRORETINOGRAPHIC USE AND METHOD OF APPLICATION

BACKGROUND OF THE INVENTION

Electroretinographic (ERG) recordings are physiologic measurements of the eye (human or animal) in response to optical stimulation. Electrodes placed on or near the eye can sense the neurological activity of the retina. The potentials so recovered are very small, ranging from a few micro-volts to a few hundred micro-volts. By analysis of the signals, disease or injury of the eye can be diagnosed.

The International Society for Clinical Electrophysiology of Vision (ISCEV), in its "Standard for full-field clinical electroretinography" provides recommendations for the use and types of electrodes. Conductive fibers, corneal wicks, foils, conjunctival loops, and contact lens types are referenced.

Contact lens electrodes are known to provide the highest amplitude and provide the most stable or repeatable results. The greatest signal is found at the center, and gradually lessens toward the periphery of the eye. But corneal electrodes can be painful, and too difficult for some subjects.

The means for making electrodes had proceeded on an ad hoc basis since its earliest beginnings. Most of the pioneering development was conducted in research centers, and as the value of the methods to diagnose retinal disease was recognized, it has become an important clinical tool.

Examples of ERG electrodes that relate to this design are:
- Described as a transparent corneal cup, it is used in conjunction with a conductive fluid (U.S. Pat. No. 4,131,113).
- Owing to its simplicity and economy, a corneal wick described by W W Dawson, G L Trick and C A Litzkow, is popularly referred to as the "DTL electrode" (U.S. Pat. No. 4,417,581).
- Not quite a contact lens, because it can have a central aperture hole, a conductive gel corneal electrode is cast to shape with an attached flexible wire lead (U.S. Pat. No. 4,735,207).
- At the far end of this category, scleral electrodes record biopotentials as far from the cornea to avoid issues of damage or irritation (U.S. Pat. No. 4,874,237).
- A second type of scleral electrode was described that is formed of a stiff coaxial cable loop that is inserted under the lower eyelid (U.S. Pat. No. 5,154,174).
- Combining both corneal and scleral electrode support in a large contact lens, a device that also provides a fixture for the illumination optics is useful for animal studies because it prevents blinking (U.S. Pat. No. 5,297,554).
- An array of electrodes in a corneal lens combined with multifocal ERG is applied in a retinal mapping application (U.S. Pat. No. 7,384,145).
- Combining a flexible coaxially shielded interconnecting cable and a spherical button electrode, the assembly can be packaged individually, or in an array. The purpose of the spherical form of the electrode is to help anchor it in one spot (U.S. Pat. No. 7,596,400).

When corneal electrodes are used, topical anesthesia may be required as the cornea is very sensitive. It may also be necessary to apply a lubricating solution between the cornea and the electrode.

Coaxial cables are useful to shield the voltage measurement from outside interference. However, coaxial cables are prone to a source of noise that is piezo and triboelectrically generated. As the cable is flexed, the dielectric between the center conductor and the shield is alternately squeezed or stretched, electrical charges are generated. Special low noise cables may have a graphite inner lining to reduce triboelectric noise, but the piezo effects can remain.

To limit the flexing of the cables, attachment of the lead wires near the eye is necessary. This has to be done with great care to avoid pulling the electrode(s) out of alignment. This is in spite of movement of the eye or blinking. This can be very uncomfortable to the subject and painful to remove.

SUMMARY OF THE INVENTION

A springy wire lead is fixtured in front of the eye. The springy wire lead is formed into a U-shape, with a smooth bead electrode positioned at the bottom of the U-form. The electrode assembly is held at about a 45-degree angle from vertical, so that the bead electrode makes contact with the eye at the junction between the lower edge of the cornea at the sclera margin next to the lower eyelid. With the electrode so disposed, the eye is free to move normally, and the subject may blink without interfering with the placement and alignment of the electrode.

The electrode fixture could be in the form of a pair of spectacles, or a fixed mount such as used in a Ganzfeld ERG apparatus. The fixture can include preamplification and EMI shielding. This eliminates the flexible interconnect to the electrode and the attendant noise that might be generated. Other forms of fixed mounts could be adapted to fixture an electrode in a similar manner.

The advantage of such an arrangement is the speed at which a subject for an ERG assessment can be fitted for measurement. In the case where glasses are used as the fixture, the subject simply looks up, and puts on the glasses.

An additional aspect of the invention is the means to detect if the electrode lead is broken. The electrical continuity of the electrode loop can be sensed. This would alert the operator to effect corrective action.

DETAILED DESCRIPTION OF THE INVENTION

Figure 1:
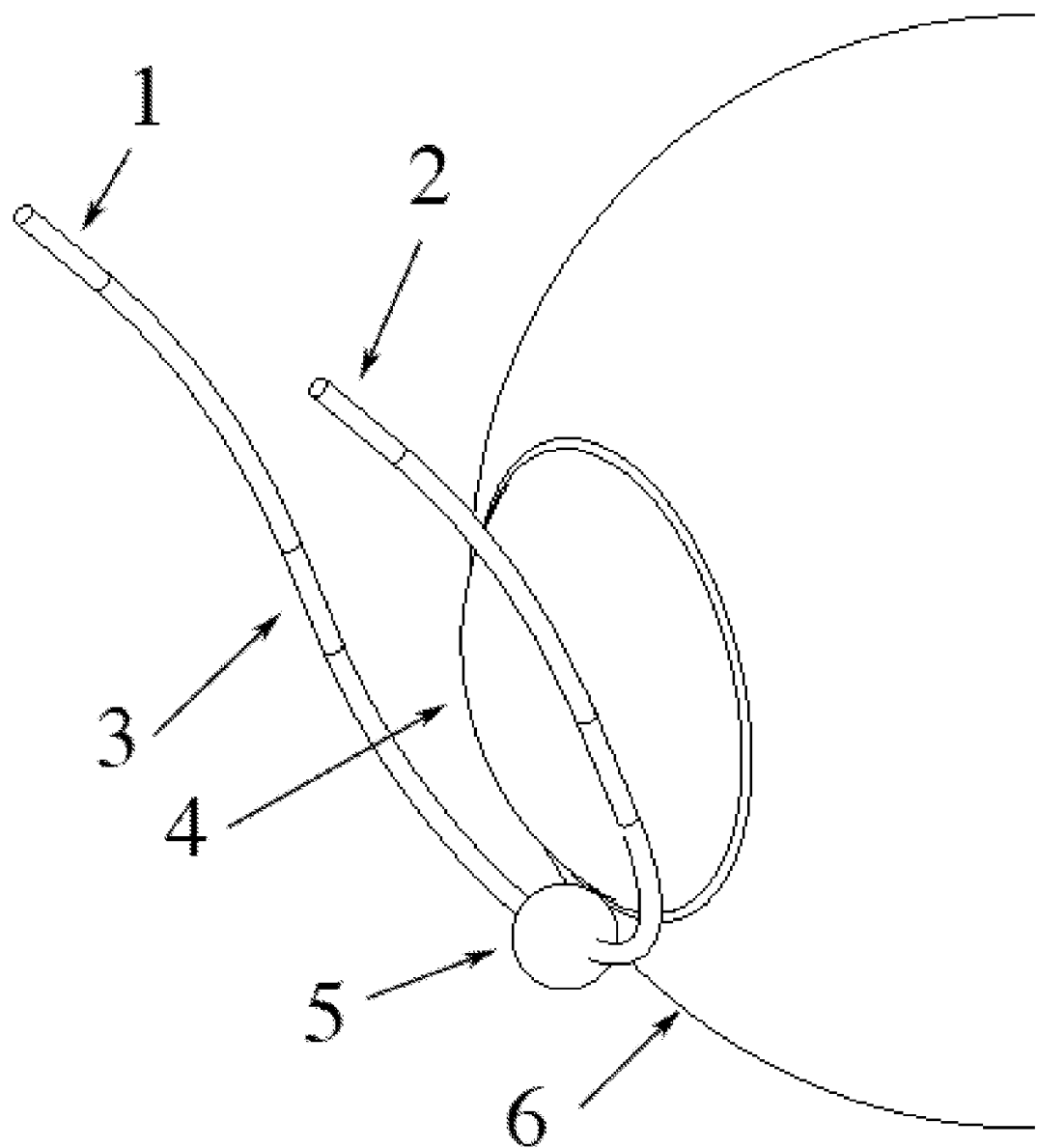
FIG. 1 is a perspective close up view of the electrode assembly in contact with the eye.
Figure 2:
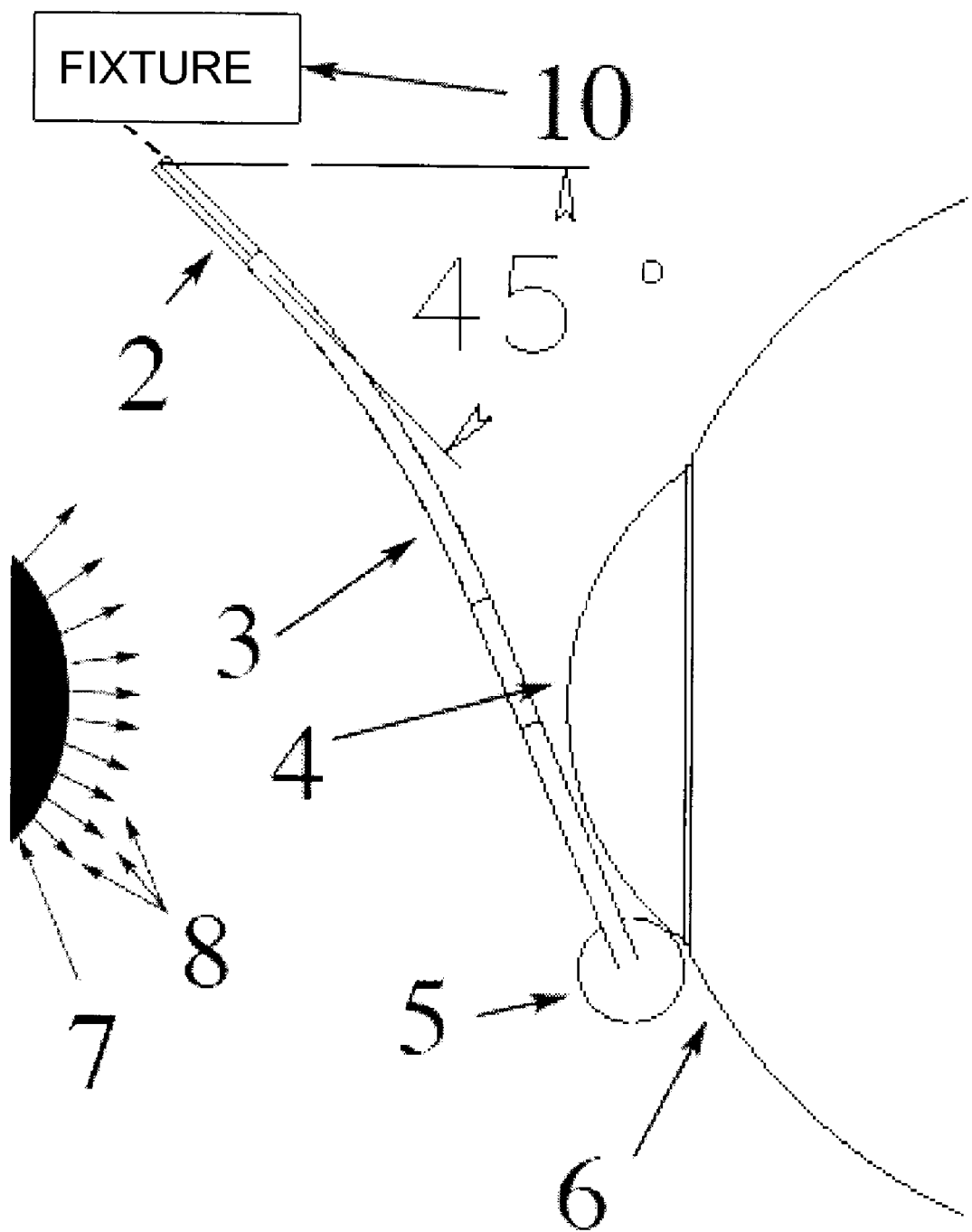
FIG. 2 is a side view of the electrode assembly showing the mount angle and the contact of the electrode bead to the corneal margin.
Figure 3:
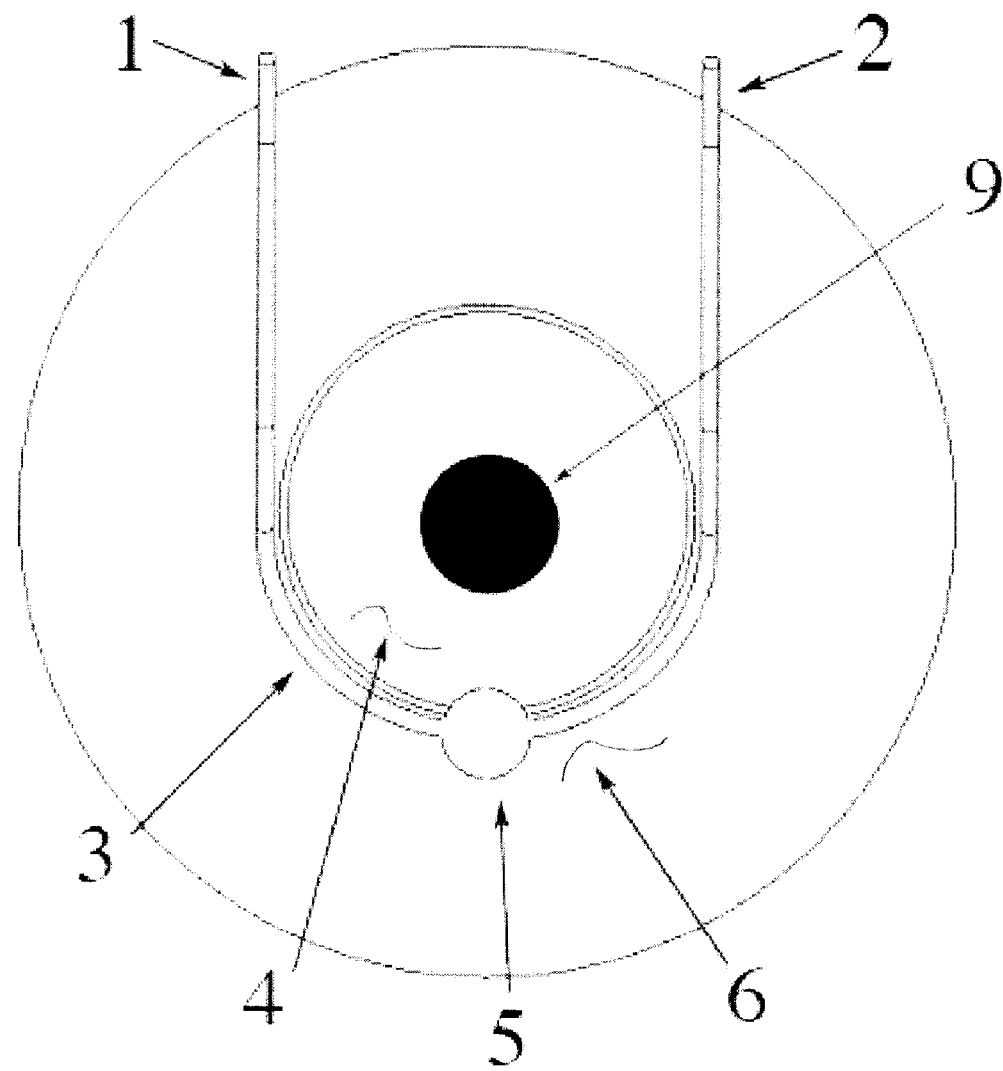
FIG. 3 is a front view showing the width of the electrode U-shape relative to the eye, and clearance to the pupil and the ERG illumination path.

A wire of about 43 mm free length is held in a fixture such that the wire is shaped into a U-form with the terminal ends 1, 2 of the electrode assembly 3 spaced about 10 mm apart. A smooth silver bead shaped electrode 5 of about 2 mm diameter is threaded onto the lead wire and positioned at the bottom of the U-form. As seen in FIGS. 1-3, the electrode assembly 3 is held at about a 45-degree angle from vertical, so that the bead shaped electrode 5 makes contact with the eye at the junction between the lower edge of the cornea 4 at the sclera 6 margin. With the electrode assembly 3 so disposed, the subject's eye is free to move normally, the subject's pupil 9 is not obscured, the subject may blink without interfering with the placement and alignment of the electrode assembly 3 and the rays 8 of the ERG illumination light source 7 are not obscured.

The wire is preferably made of a super-elastic alloy, such as Nitinol, an alloy of nickel and titanium. This material can be repeatedly flexed to an extreme degree and the electrode will return to its original form. It also is very immune to stress fracture. The wire may alternatively be made of conductive elastomer, conductive plastic, conductive glass capillary, or a conductive glass fiber.

As indicated above, the electrode assembly 3 is supported in a fixture 10 by its terminal ends 1,2 so that the U-form is angled about 45 degrees from vertical. Ideally, the mount is adjusted such that the electrode is held in contact with the eye with about 2 mm of engagement. The electrode assembly 3 may be mounted to many fixtures 10 including a spectacle mount, goggles, a hand held appliance, a fixed head rest such as a Ganzfeld illuminator or any other fixture 10 capable of being used for enabling the proper position of the assembly and contact of the electrode 5 with a subject's eye as disclosed herein.

The electrode assembly 3 will flex on contact of the bead shaped electrode 5 to the eye. The forces placed on the eye must be limited to avoid distorting the cornea 4, and thereby distorting the vision or worse yet, injuring the subject. A Nitinol wire of about 0.4 mm diameter yields a good compromise of stiffness and flexibility.

The length of the wire, the spacing between the terminal ends 1, 2, and the mount angle can be altered as needed to make the alignment desired to the subject's eye.

The bead shaped electrode 5 is preferably made of silver, or plated with silver, which acts to inhibit microbial growth. Alternatively, the electrode could be coated with an antibacterial agent. The electrode assembly can be autoclaved and reused. The electrode 5 may alternatively be made of any silver alloy, gold alloy, platinum alloy, titanium alloy, or a base metal alloy with a protective coating. Alternatively, the electrode 5 is fabricated from a conductive elastomer, a conductive plastic, or a conductive glass.

The bead shaped electrode 5 could be left to be free to rotate like a bearing on the wire, or it could be bonded to the wire. Simple gravity could be adequate to maintain the position of the bead at the bottom of the U-form.

A means to monitor the integrity of the electrode loop (electrode assembly 3) should be implemented to assure the safety of the user. Although it should be obvious if one end of the electrode assembly is broken from the mount, it is a fairly simple matter to test the continuity of the connections.

The ERG signals require amplification in order to be recorded. A common method to accomplish this is a non-inverting amplifier. It has a high input impedance and can be tailored to have the gain and bandwidth needed for the application. Devices are available for the amplifier that operate from a single power supply, and can amplify signals near or including the zero potential (a property called the common mode voltage range). This is useful for battery operation and economy of construction.

One means of dealing with signals that are very close to the negative, or in this case, zero supply rail, is to very slightly bias the amplifier input so it stays positive of the zero point. In this application, the bias needs to be only a few millivolts to compensate for any input offset voltage of the amplifier.

The ERG standards recommend that the input impedance of the electrode amplifier be on the order of 10 Meg ohms. This impedance can be used with the bias network to generate a few millivolts offset.

Figure 4:
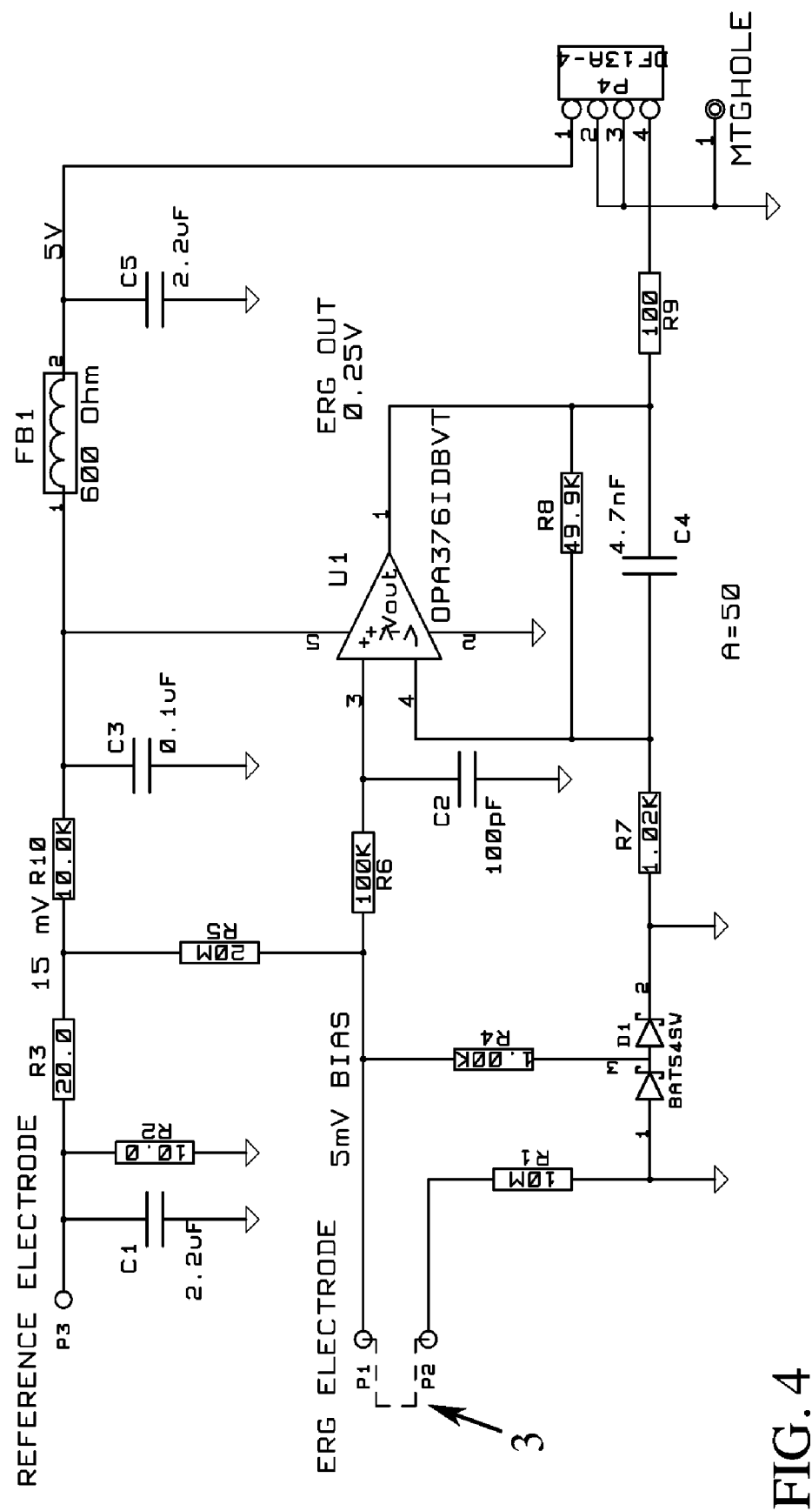
FIG. 4 is a schematic of an electrode preamplifier and the bias means to sense continuity of the electrode loop.

The schematic at FIG. 4 illustrates one embodiment of an amplifier with the desired functions. R1 is a 10 M resistor connected to node P2 of the electrode wire, and together with R5 establishes the input impedance requirement. The other end of the electrode wire is the node P1, and it completes the connection to the amplifier input filter (R6, C2), the offset bias (R5), and the input protection network (R4, D1). The amplifier (U1) is configured with a voltage gain of 50 V/V by the feedback network (R7, R8). C4 further acts on the amplifier feedback to limit the amplifier bandwidth above 600 hertz.

The voltage divider formed by R5 (connected to a 15 mV bias) and the input impedance (R1), create a 5 mV input bias. A reference electrode is biased (voltage divider at R2, R3) to the same degree of offset so as to cancel any potential differential with the electrode assembly 3. The reference electrode is connected to the subject by any number of means (nose bridge, forehead touch bar, temple contacting glasses, etc.) and would be well known to any one skilled in the art of ERG methods.

The voltage gain of the amplifier develops a 250 mV output, upon which the amplified ERG signals are superimposed. A very small current (500 pA) from R5 passes through the electrode loop and then R1. If the connection to the electrode loop is broken, the input bias will then rise to 15 mV, and the amplifier output rises to about 0.75 volts.

Any time the amplifier output is found to be significantly higher than 0.25 volts, the electrode connection can be considered to be faulty. Anyone skilled in the art could develop alternative topologies that pass a current through the electrode to establish continuity and make the ERG measurements.

The preceding description and the accompanying drawing figures describe the present invention. Variations are possible without departing from the spirit and scope of this invention.

What is claimed is:

1. A conductive electrode assembly for the measurement of corneal electroretinographic (ERG) signals, the electrode assembly comprising:
    a bead shaped electrode adapted to contact a subject's eye; and
    a flexible wire supporting the bead shaped electrode, wherein the wire is configured to be mounted to enable the bead shaped electrode to make contact with a junction between a cornea and sclera of the subject's eye.

2. The electrode assembly of claim 1 wherein the wire is constructed of a super-elastic alloy, conductive elastomer, conductive plastic, conductive glass capillary, or a conductive glass fiber.

3. The electrode assembly of claim 1 wherein the electrode is fabricated from a silver alloy, a gold alloy, a platinum alloy, a titanium alloy, or a base metal alloy with a protective coating.

4. The electrode assembly of claim 1 wherein the electrode is fabricated from a conductive elastomer, a conductive plastic, or a conductive glass.

5. The electrode assembly of claim 1 wherein the electrode is fabricated from an insulating material with a conductive coating.

6. The electrode assembly of claim 1 wherein the electrode is fixed to the flexible wire.

7. The electrode assembly of claim 1 wherein the electrode is free to move on the flexible wire, or is constrained to only rotate.

8. The electrode assembly of claim 1 wherein the flexible wire is shaped into a U-form with the electrode mounted at the bottom of the U shape.

9. The electrode assembly of claim 1 wherein the wire is adapted to be mounted to a fixture at an angle so as to align the electrode against the subject's eye but not obscuring a pupil of the subject's eye or an ERG illumination light source.

10. The electrode assembly of claim 1 wherein the electrode assembly is constructed to sense current, voltage, resistance or impedance.

11. An electrode assembly for measuring electroretinographic (ERG) signals from a subject's eye, the electrode assembly comprising:
   an electrode adapted to contact a subject's eye; and
   a wire supporting the electrode between first and second ends of the wire, wherein the first and second ends of the wire are configured to be mounted to enable the electrode to make contact with a junction between a cornea and sclera of the subject's eye.

12. The electrode assembly of claim 11 wherein the wire is constructed of a flexible material.

13. The electrode assembly of claim 11 wherein the electrode is bead shaped.

14. The electrode assembly of claim 11 wherein the electrode is fixed to the wire.

15. The electrode assembly of claim 11 wherein the electrode is adapted to rotate about the wire and/or move along the wire.

16. The electrode assembly of claim 11 wherein the wire is adapted to be mounted to a fixture.

17. A method of applying an electrode to a patient's eye, the method comprising:
   providing an electrode assembly for contacting a subject's eye, the electrode assembly including an electrode and a wire supporting the electrode between first and second ends of the wire; and
   mounting the electrode assembly to enable the electrode to make contact with a junction between a cornea and sclera of the subject's eye.

* * * * *